(12) United States Patent
Revie et al.

(10) Patent No.: US 6,245,113 B1
(45) Date of Patent: Jun. 12, 2001

(54) CENTRALIZER

(75) Inventors: Ian Crawford Revie, Boroughbridge; Bruno Hiernard, Hampshire, both of (GB)

(73) Assignee: Johnson & Johnson Medical Ltd. (GB)

(*) Notice: Subject to any disclaimer, the term of this patent is extended or adjusted under 35 U.S.C. 154(b) by 0 days.

(21) Appl. No.: 09/414,219

(22) Filed: Oct. 7, 1999

(30) Foreign Application Priority Data

Oct. 8, 1998 (GB) .................................... 9821993

(51) Int. Cl.$^7$ ...................................... A61F 2/36
(52) U.S. Cl. .................... 623/23.46; 623/23.48; 623/23.19
(58) Field of Search .............. 623/23.48, 23.19, 623/23.37, 23.46, 23.25, 23.15; 606/62, 92, 95, 86

(56) References Cited

U.S. PATENT DOCUMENTS

| | | | |
|---|---|---|---|
| 4,064,567 | * 12/1977 | Burstein et al. | 623/23.25 |
| 5,080,680 | * 1/1992 | Mikhail et al. | 623/23.46 |
| 5,163,963 | * 11/1992 | Hewka et al. | 623/23.46 |
| 5,197,990 | * 3/1993 | Lawes et al. | 623/23.48 |
| 5,425,768 | * 6/1995 | Carpenter et al. | 623/23.46 |
| 5,443,523 | * 8/1995 | Mikhail | 623/23.46 |
| 5,658,351 | * 8/1997 | Dudasik et al. | 623/23.46 |
| 5,755,793 | * 5/1998 | Smith et al. | 623/23.46 |
| 5,997,581 | * 12/1999 | Khalili | 623/23.48 |

* cited by examiner

Primary Examiner—Pedro Philogene
(74) Attorney, Agent, or Firm—John S. Wagley

(57) ABSTRACT

A centralizer (1) is provided with a hollow body (2) and a plurality of equally spaced arms (4). The arms (4) extend in the form of cup handles from the hollow body (2). Each arm (4) has a variable cross-section along its length with the cross-section becoming increasingly ovoid towards one end of the arm (4).

20 Claims, 2 Drawing Sheets

CENTRALIZER

BACKGROUND OF THE INVENTION

This invention relates to a centraliser for a prosthetic implant, in particular a prosthetic femoral stem for implantation in a patient's femur for hip replacement surgery.

Centralisers or spacers are provided for fitting to the distal end of a femoral hip replacement stem in order to keep the implant stem away from the internal surface of the cavity of the bone in which the stem is to be inserted. In the case of stems which are cemented in the bone cavity, there is a space between the stem and the internal surface of the cavity of the bone in which bone cement is placed. Controlling the position of the stem within the surrounding bone cement mantle is vital to the long-term survivability of the replacement joint. Cement can be deposited in the bone cavity and the stem with the attached centraliser is then inserted. It is important to try to obtain an even and intact cement mantle around the stem.

Known centralisers are in the form of caps which fit over the distal end of the stem and centralisers which are fixed inside the drilled end of a stem. Centralisers are also known, for example as described in U.S. Pat. No. 4,658,351, which are of ring form which can have a tapered inner surface corresponding to the tapered surface of the distal end of the femoral stem on which the centraliser is located.

U.S. Pat. No. 3,793,650 describes a centraliser or spacer which has spring members which extend from the stem for contact with the wall of the bone cavity.

European patent No. EP0427444B describes a centraliser or spacer in the form of a cap for insertion on the end of a hip stem with fins or wings extending outwardly from the cap which are adapted to fold circumferentially and inwardly towards the body portion of the cap.

BRIEF SUMMARY OF THE INVENTION

According to the present invention, there is provided a centraliser for use on a prosthetic component to be inserted in a bone cavity, the centraliser comprising a hollow body with a plurality of spacer means projecting from the body, wherein the spacer means are in the form of arms extending outwardly from the hollow body and having a variable cross-section along the length of the arms.

The hollow body may have one open end and be in the form of a cap. Alternatively, the hollow body may have two open ends and be in the form of an elongated ring. The hollow body may be in the form of a truncated cylinder.

Preferably, each arm has a first end attached to the hollow body. A second end of each arm may also be attached to the hollow body.

Preferably, the arms have a cross-section which varies from a circle becoming increasingly ovoid along the length of the arms.

Preferably, the plurality of arms are equally spaced circumferentially around the hollow body. There may be three equally spaced arms.

Preferably, the arms are attached to the hollow body such that they extend parallel to the central axis running through the hollow body.

BRIEF DESCRIPTION OF THE SEVERAL VIEWS OF THE DRAWINGS

An embodiment of a centraliser in accordance with the present invention is now described by means of example only, with reference to the drawings in which.

DETAILED DESCRIPTION OF THE INVENTION

Figure 1:
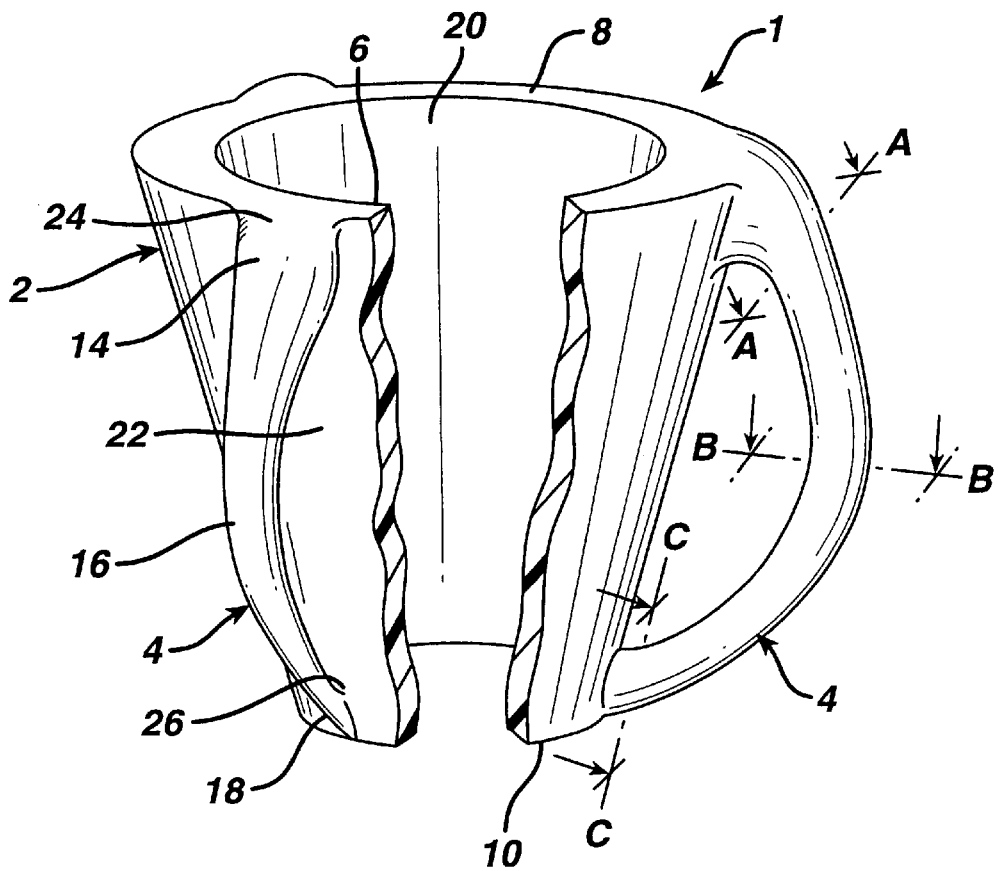
FIG. 1 is a perspective view of a centraliser in accordance with an embodiment of the present invention.
Figure 2:
FIG. 2 is a cross-section of an arm of the centraliser of FIG. 1 through line A—A.
Figure 3:
FIG. 3 is a cross-section through an arm of the centraliser of FIG. 1 through line B—B.
Figure 4:
FIG. 4 is a cross-section of an arm of the centraliser of FIG. 1 through line C—C.

Referring to FIGS. 1, 2, 3, and 4, an embodiment of the present invention is shown as a centraliser 1 with a hollow body 2 and a plurality of arms 4 extending outwardly from the body 2.

The body 2 is of elongated annular form and may be in the form of a truncated hollow cylinder. The body 2 has an outer surface 22 and an inner surface 20. The inner and outer surfaces 20, 22 are joined by an upper edge 6 of the body 2 and a lower edge 11 of the body 2. The upper edge 6 of the body 2 is generally circular and has a greater diameter than the lower edge 11 of the body which is also generally circular.

The hollow body 1 had one open end at lower edge 10 and is in the form of a cap.

In this example, the centraliser 1 has three arms 4 equally spaced around the body 2. Each arm 4 has a first end 24 which is attached to the body 2 adjacent the upper edge 6 of the body 2. The second end 26 of each arm is attached adjacent the lower edge 11 of the body 2. Each arm 4 curves outwardly from the body 2 to form a D-shape. The arms 4 extend parallel to a central axis through the body 2. The arms 4 resemble cup handles equally spaced around the body 2.

Each arm 4 has a cross-section which varies from the first end 24 to the second end 26 of each arm 4. A top portion 14 of each arm 4 has a generally circular cross-section which provides stiffness to the arm 4. A mid-portion 16 of each arm 4 has an increasingly ovoid cross-section and a lower portion 18 of each arm 4. has a thin ovoid cross-section. The change in cross-section along the arms 4 increases the flexibility of the arms 4 towards the second end 26 of the arms 4.

It is an aim of the present invention to provide a centraliser which fits a range of prosthetic hip stems with no provision made for stem subsidence within the centraliser. The centraliser 1 is formed of a plasticised PMMA material which is capable of bonding with a surrounding PMMA cement mantle.

In the present example, the centraliser 1 is designed to fit in bone cavities of 10 mm–20 mm diameter at 2 mm increments. The size of the centraliser 1 is linked with the stem size and the outer form linked with the distal reamers to be used with the cemented stem.

The centraliser 1 wedges on a distal end of a femoral stem with the femoral stem contacting the inner surface 20 of the centraliser 1 at about 10 mm–15 mm from the distal end of the stem.

The centraliser 1 can fit into bone cavities ranging from the stem size plus a 2 mm cement mantle to the stem size plus a 4 mm cement mantle. This variation in size can arise if a surgeon decides to undersize the stem for a prepared bone cavity. The centraliser 1 adapts to a varying size of bone cavity by having flexible arms 4. The flexibility of the arms 4 is restricted to prevent undersizing of the cement mantle, in other words, the minimum cement mantle should be 2 mm at the distal end.

The centraliser 1 of the present invention achieves the above requirements by having a plurality of arms 4 which give constrained flexion due to the variable cross-section along the arms 4.

As the arms 4 are constrained at both ends 24, 26, this ensures that the centraliser 1 provides resistance to insertion in undersized medullary cavities. This ensures that surgeon's choice of canal and stem size is controlled and that the stem size to canal size is matched. However, should the surgeon require to oversize the stem for a given medullary cavity, he can do so by overcoming the resistance to the undersized arms 1 of the centraliser 1.

Figure 1A:
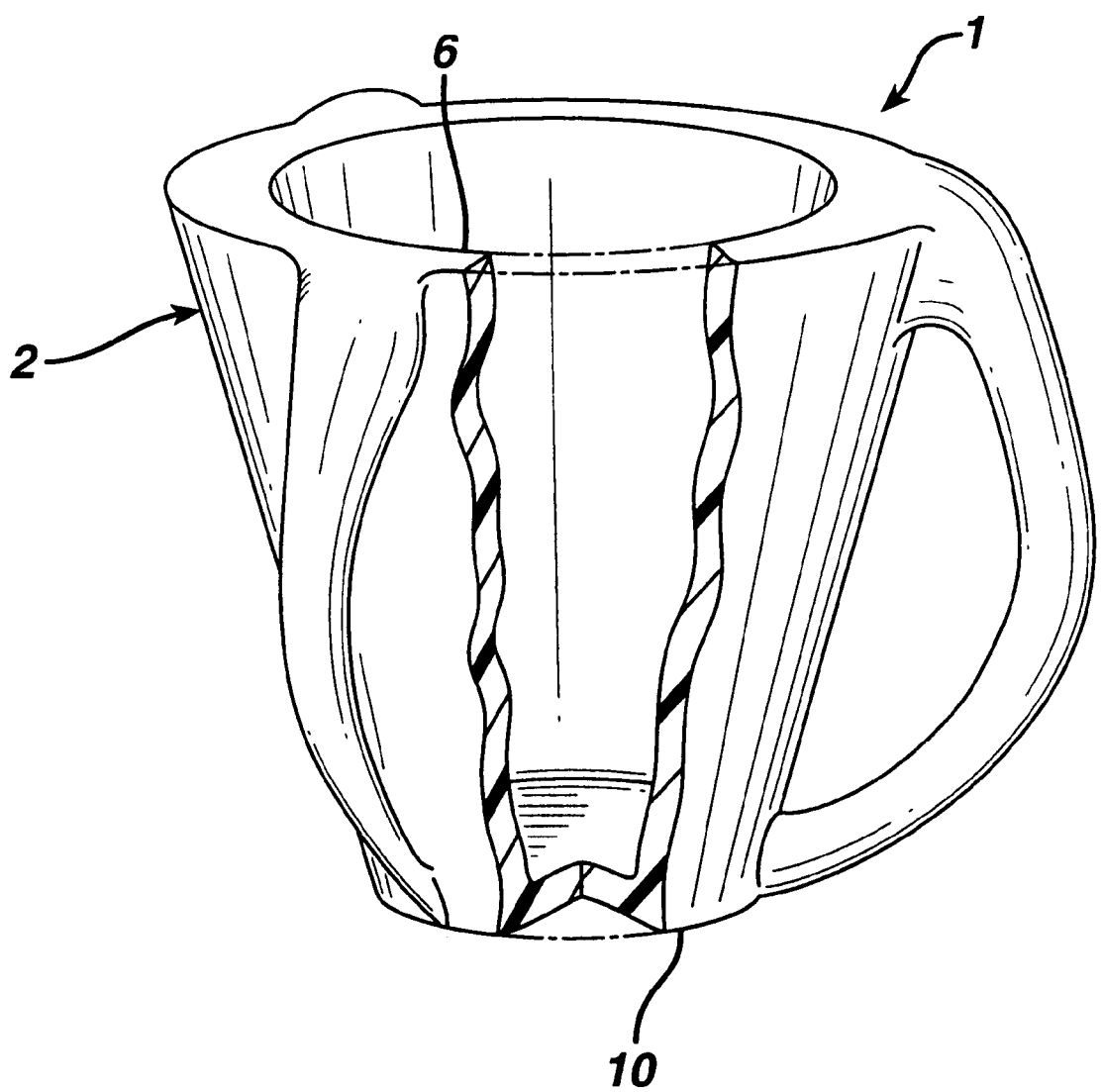
FIG. 1A is a perspective view of a centraliser in accordance with another embodiment of the present invention.

Referring to FIG. 1A another embodiment of the present invention is shown as a centraliser 1 with a hollow body 2 and a plurality of arms extending outwardly from the body 2. All element of the centraliser 1 of FIG. 1A correspond to those of the centraliser 1 of FIG. 1, except that the hollow body 1 of FIG. 1A has two open ends, one at lower edge 10 and one at upper edge 6. The centraliser 1 is in the form of an elongated ring.

Improvements and modifications can be made to the foregoing without departing from the scope of the present invention.

What is claimed is:

1. A centraliser for use on a prosthetic component to be inserted in a bone cavity, the centraliser comprising a hollow body with a plurality of spacer means projecting from the body, wherein the spacer means are in the form of arms extending outwardly form the hollow body, at least one of the arms having a first portion connected to the body, a second portion spaced from the first portion and connected to the body and a third portion connecting the first portion and the second portion, the third portion spaced from the body and defining an opening therebetween.

2. A centraliser as in claim 1, wherein at least one of the arms has a variable cross section along the length thereof.

3. A centraliser as in claim 1, wherein the plurality of arms are equally spaced circumferentially around the hollow body.

4. A centraliser as in claim 1, wherein at least one of the arms are attached to the hollow body such that they extend parallel to the central axis running through the hollow body.

5. A centraliser as in claim 1, wherein the hollow body has one open end and is in the form of a cap.

6. A centraliser as in claim 1, wherein the hollow body has two open ends and is in the form of an elongated ring.

7. A centraliser as in claim 1, wherein at least one of the arms has a cross section which varies from a circle becoming increasingly ovoid along the length of the arms.

8. A centraliser for use on a prosthetic component to be inserted in a bone cavity, the centraliser comprising a hollow body with a plurality of spacer means projecting from the body, wherein the spacer means are in the form of arms extending outwardly form the hollow body.

9. A centraliser as in claim 8, wherein at least one of the arms has a variable cross section along the length thereof.

10. A centraliser as in claim 8, wherein at least one of the arms are attached to the hollow body such that they extend parallel to the central axis running through the hollow body.

11. A centraliser as in claim 8, wherein the hollow body has one open end and is in the form of a cap.

12. A centraliser as in claim 8, wherein the hollow body has two open ends and is in the form of an elongated ring.

13. A centraliser as in claim 8, wherein at least one of the arms has a cross section which varies from a circle becoming increasingly ovoid along the length of the arms.

14. A centraliser for use on a prosthetic component to be inserted in a bone cavity, the centraliser comprising a hollow body with a plurality of spacer means projecting from the body, wherein the spacer means are adapted to provide restricted flexibility to provide for a minimum cement mantle of 2 millimeters at the distal end of the prosthetic component.

15. A centraliser as in claim 14 wherein the spacer means are in the form of arms extending outwardly from the hollow body and wherein at least one of the arms has a variable cross section along the length thereof.

16. A centraliser as in claim 14, wherein the spacer means are in the form of arms extending outwardly from the hollow body and wherein the plurality of arms are equally spaced circumferentially around the hollow body.

17. A centraliser as in claim 14, wherein the spacer means are in the form of arms extending outwardly from the hollow body and wherein at least one of the arms are attached to the hollow body such that they extend parallel to the central axis running through the hollow body.

18. A centraliser as in claim 14, wherein the hollow body has one open end and is in the form of a cap.

19. A centraliser as in claim 14, wherein the hollow body has two open ends and is in the form of an elongated ring.

20. A centraliser as in claim 14, wherein the spacer means are in the form of arms extending outwardly from the hollow body and wherein at least one of the arms has a cross section which varies from a circle becoming increasingly ovoid along the length of the arms.

* * * * *